US006843951B2

(12) United States Patent
Vogel et al.

(10) Patent No.: US 6,843,951 B2
(45) Date of Patent: Jan. 18, 2005

(54) METHOD AND APPARATUS FOR MAKING A DENTAL DEVICE OR THE LIKE

(76) Inventors: Dan Vogel, 240 Gregory Rd., Franklin Lakes, NJ (US) 07417; Richard J. Pitz, 400 E. 54th St., New York, NY (US) 10022

( * ) Notice: Subject to any disclaimer, the term of this patent is extended or adjusted under 35 U.S.C. 154(b) by 90 days.

(21) Appl. No.: 10/161,985

(22) Filed: Jun. 1, 2002

(65) Prior Publication Data

US 2003/0222365 A1 Dec. 4, 2003

(51) Int. Cl.⁷ .................. B29C 35/08; B29C 33/40; B28B 13/06
(52) U.S. Cl. ............... 264/405; 264/494; 264/101; 264/334; 264/337; 249/54
(58) Field of Search ............... 264/16, 17, 18, 264/19, 20

(56) References Cited

U.S. PATENT DOCUMENTS

| | | | |
|---|---|---|---|
| 2,423,330 A | 7/1947 | Levine | 264/17 |
| 3,001,240 A | 9/1961 | Emerick | 264/17 |
| 3,663,141 A * | 5/1972 | Clenet et al. | 425/175 |
| 3,905,106 A | 9/1975 | Costa et al. | 433/213 |
| 4,562,882 A * | 1/1986 | Alleluia | 164/529 |
| 4,571,188 A | 2/1986 | Hamilton | 433/226 |
| 5,000,687 A | 3/1991 | Yarovesky et al. | 433/180 |
| 5,040,964 A | 8/1991 | Oppawsky et al. | 264/16 |
| 5,104,591 A | 4/1992 | Masuhara et al. | 264/16 |
| 5,348,475 A | 9/1994 | Waknine et al. | 264/16 |
| 5,667,386 A | 9/1997 | Black et al. | 433/213 |
| 6,386,865 B1 | 5/2002 | Suh et al. | 433/27 |
| 6,660,194 B1 * | 12/2003 | Arita | 264/17 |

* cited by examiner

Primary Examiner—Stephen J. Lechert, Jr.
(74) Attorney, Agent, or Firm—Epstein Drangel Bazerman & James, LLP (57) ABSTRACT

The method of making a dental device or the like which involves starting with a pattern of the device to be made, closely surrounding that pattern with a settable material to form a unit with the pattern, separating the unit and removing the pattern therefrom, filling the thus produced space with settable material of the type desired for the ultimate device, setting that material and removing the set material constituting the device to be made, and in particular utilizing a retention device to enclose the settable materials and other contents. The process is particularly useful when the device is to be made of a light-sensitive material, in which case the retention device and the first-used settable material are light-transmissive and the retention device preferably focuses light on the material to be set.

19 Claims, 7 Drawing Sheets

METHOD AND APPARATUS FOR MAKING A DENTAL DEVICE OR THE LIKE

BACKGROUND

This invention pertains generally to pressure molding of fluid materials and particularly using light energy to cure such materials. It also pertains to molds fabricated from self curing optically clear materials so that fluid materials cured with light energy may be used in conjunction with such molds.

Various types of dental restorative materials that use light energy to change from a plastic state to a fused or "cured" state are used in dentistry. These materials may either be placed incrementally in the tooth and cured in layers or fabricated in the laboratory on a model made from an impression taken in the patient's mouth.

In the first instance where the curing takes place in the patient's mouth, control becomes a problem. Such control incorporates ability to maintain a dry field, to completely cover all the prepared tooth surface (close the margins), maintain a homogeneous material layer without incorporating spaces which have no restorative material, proper contact, contour size, shape, occlusal harmony and depth of cure to name a few. The advantages are that it is quick, has a reasonable success rate and is of moderate expense. It satisfies the patient's desire for an aesthetic restoration.

In the second instance the indirect method which requires a model made from an impression allows for complete control over the size, shape, contour, contact, shade and occlusal harmony to name a few. The disadvantages are that the model is completely dependant upon an accurate impression, an accurate stone model (no bubble, cracks, etc.), requires more time for fabrication and is much more costly.

In both instances, shrinkage of the material must be taken into consideration. In each case the material does not cure at the surface (an oxygen inhibited layer). In the first instance complete curing by tempering is not possible while in the second instance heat tempering (200–250 degrees F. for 15 minutes) gives the laboratory fabricated restoration more strength.

Laboratory fabricated composite resin inlays and/or crowns are usually assembled in an incremental fashion by placing small amounts of the appropriate colored composite in or on the stone die and light curing it followed by an additional increment until the proper configuration is accomplished. Notwithstanding the care with which the material may be placed, there is always a difference in the cure and coverage of the material in the incremental method. In addition clear modeling resins are used to prevent the instruments from sticking to the resin and ensure one layer sticks to the other. All manufacturers advise using only small amounts of the fluid as it has the tendency of reducing the strength of the cured material. This method is cured from the inside out. The light source is unidirectional and as a consequence the shrinkage is away from the margins and die surface. It requires that a separating material be placed on or in the model such that the partially cured material may be removed without breaking or mutilating the die. It is not desirable to remove the restoration prior to completion in this method as it never reseats accurately. Consequently the thickness of the restoration cannot be verified prior to curing. Spacer thickness creates a problem when the restoration is to be placed in the mouth and cured. The American Dental Association has specifications regarding cement thickness for all types of restorations. The spacer thickness cannot be controlled to a degree such that there is a reproducible specified space between the restoration and the tooth.

An additional problem with the above method is that to generate occlusal harmony, the finished product must be ground and fitted to the die. This has the problem of possible fracture or changing of the die. The laboratory technician must be extremely careful in the fabrication. Also if the shade of the restoration has to be changed, the die then becomes used again where fracture can be a problem.

Many patents have been granted whereby the materials used for the fabrication laboratory restorations are subjected to various methods to strengthen them. Vacuum, pressure under nitrogen or water, and heat are just some of them. Those methods have been used singularly or in combination. In most instances they have met the test inventors' intentions.

SUMMARY OF THE INVENTION

The invention provides for a system where a viscous material such as a dental composite is heated by various means and is injected into a mold of optically clear self curing material such as silicone or polyvinylsiloxane. This mold is contained in an optically clear glass or other such optically clear retention device that is keyed to allow for the sections of the mold to come together such that there is not rotation or gap between the sections. This will allow that no distortion of the finished product will occur. The outer surface of the retention device is formed in the manner of a focusing lens that will direct the curing light energy directly upon the material contained within the mold. The shape of the retention device can be of any shape from a sphere to any parabolic shape or configuration with the intention of the invention, such that when light energy is in use, it will focus on the mold with the greatest intensity. This will enhance the rate at which the material is cured and for the material to be cured from the outside inward. This will allow for complete curing to the surface and prevent the "oxygen inhibited layer" from forming. By using intermittent light pulses of an appropriate duration and wavelength, the composite shrinks at a prescribed rate.

The shrinkage of the material is compensated by feeder tubes filled with composite and fabricated of a material that is impervious to the light energy and thus is not cured when the light is focused on the material being molded. The feeder tubes are under pressure of at least 50–150 lbs. per square inch. This will allow for the material in the tubes to be forced into the main mold as the curing takes place and compensates for the shrinkage that is inherent to the material The mold and the retention device along with the material within the mold and feeder tubes is heated to a temperature that will maximize the reduction in viscosity for each material used in the process. This heat is maintained prior to being placed within the pressure chamber.

Once the initial light curing has taken place, the restoration is removed from the clear mold and is placed in an oven under vacuum and heated to a temperature of 200–250 degrees F. for approximately 15 minutes. This process removes any volatile molecules and strengthens the finished restoration.

BRIEF DESCRIPTION OF DRAWINGS

The accompanying drawings illustrate the invention. In such drawings.

DETAILED DESCRIPTION OF THE PREFERRED EMBODIMENT

Figure 1:
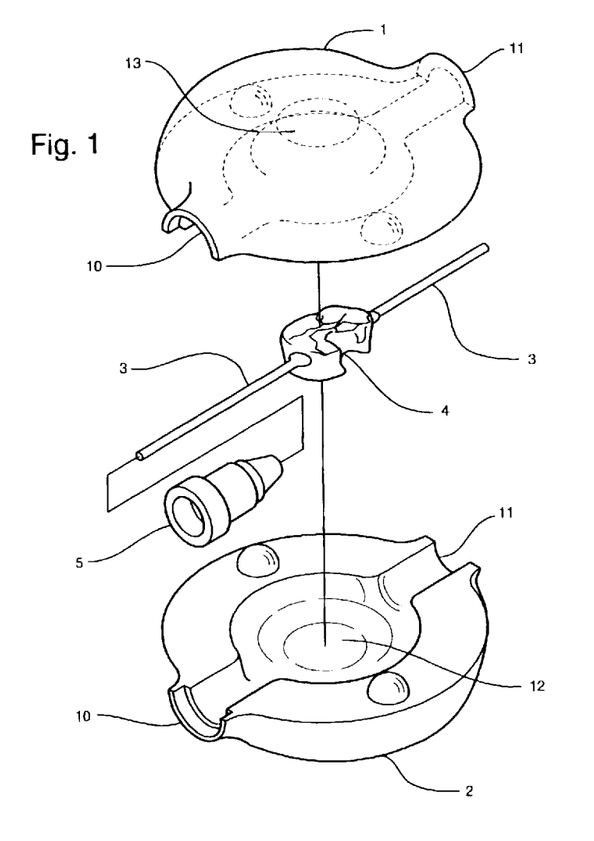
FIG. 1 is a perspective view of the separated parts of the mold retention device with the wax pattern and sprue and sprue reservoir placed between the upper and lower halves of the retention device.

FIG. 1 illustrates the device embodying the present invention. The illustrated device is comprised of an optical glass or other optical material of such configuration that the retention device (1) and (2) are fabricated in a way that there is a male and female section of equal dimension that come together so there is no gap or rotation at the mated surfaces. There are openings 1801 from one another such that a sprue reservoir (5) is attached to a sprue (3) of an appropriate material (polyethelene, etc.) so that the sprue reservoir (5) may slide along the sprue (3) to allow for maximum placement of a wax pattern (4) equidistant from openings (10) and (11). The openings (10 and 11) are of such shape that when the sections (1 and 2) are in contact with one another, the sprue reservoir (5) and the sprue (3) connected to the wax pattern (4) are held in a rigid position (FIG. 3) at opening (10). The interior area of the mated sections (1 and 2) of the retention device is spherical in shape such that each half is a duplicate of the other. There is a dimple (12 and 13) placed in each half of the retention device (1 and 2) so that when the mold that will be made in the retention device may be seated without any confusion.

Figure 2:
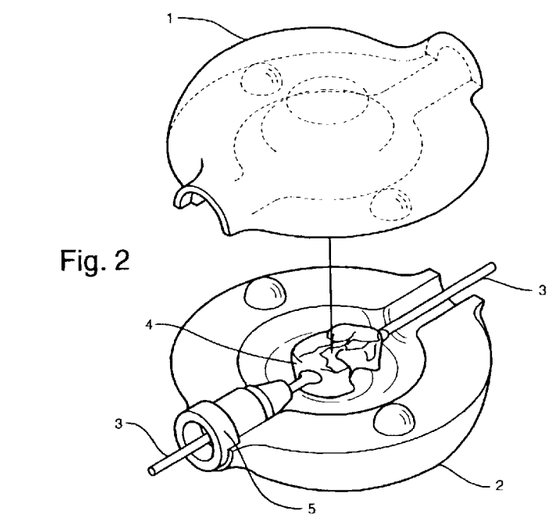
FIG. 2 shows the placement of the wax pattern and the sprue and sprue reservoir in the correct position prior to closing the upper and lower halves.
Figure 3:
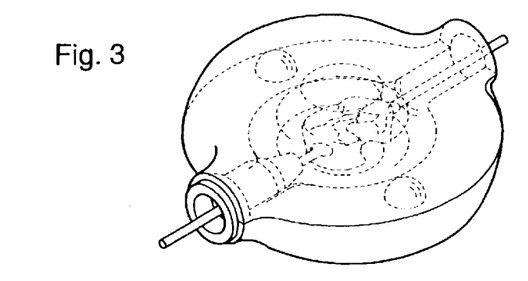
FIG. 3 is a perspective view showing the upper and lower halves of the retention device with the wax pattern, sprue and sprue reservoir in the closed position.
Figure 4:
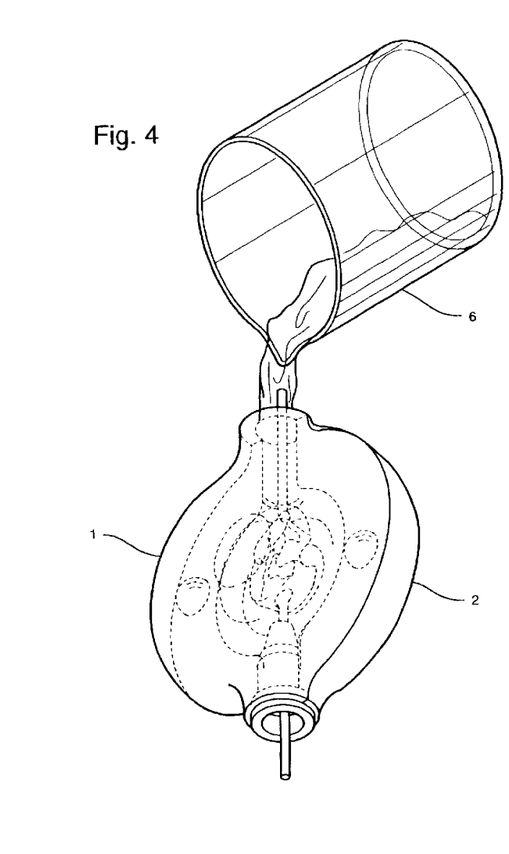
FIG. 4 is a perspective view showing the placement of the mold material through an opening opposite the sprue reservoir as shown in FIG. 3.
Figure 5:
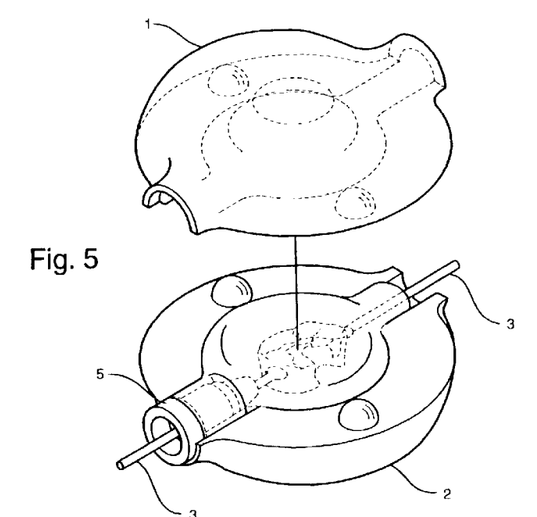
FIG. 5 is a perspective view of the separation of the retention device subsequent to the hardening of the mold material around the wax pattern, sprue and sprue reservoir as shown in FIGS. 2 and 3.
Figure 6:
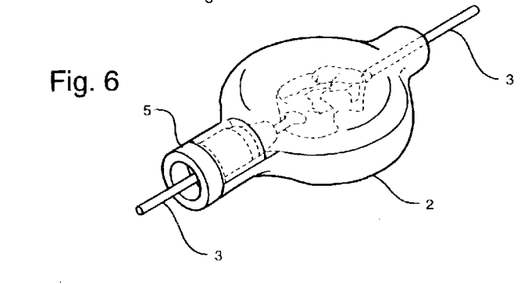
FIG. 6 is a perspective view of the mold without the surrounding retention device and showing the components as in FIG. 2.
Figure 7:
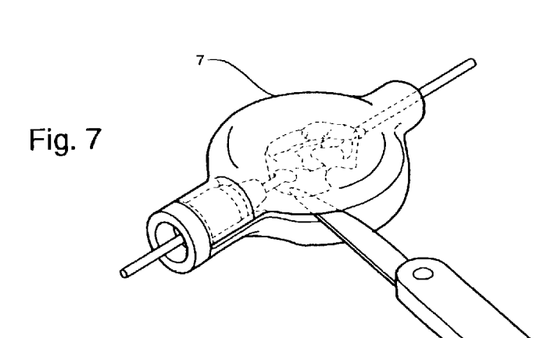
FIG. 7 is a perspective view of the separation of the mold as in FIG. 6 with a sharp instrument-such that the mold is separated in two equal parts.
Figure 8:
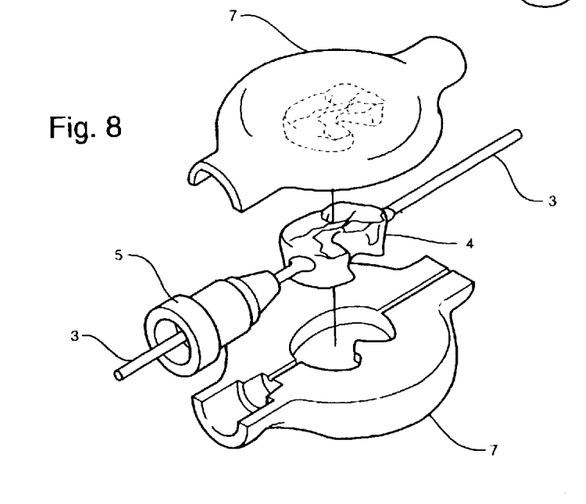
FIG. 8 is an exploded perspective view showing the mold separated in two equal parts so that the components as shown in FIG. 2 may be removed.

When the parts (1 and 5) as shown in FIG. 1 are placed together as shown in FIGS. 2 and 3, and secured, opening (11) is available for placement of the mold material (6) that may be poured or injected into the opening so that it may completely fill the area surrounding the wax pattern (4) that is held by the sprue (3) and the sprue reservoir (5). This material is a clear self setting either polyvinylsiloxane or silicone but not limited to such materials. Upon setting of the mold material, the retention device (1 and 2) is separated and the hardened mold material (7) is removed. The mold is cut into two separate equal parts and the wax pattern (4), the sprue (3) and the sprue reservoir (5) are removed as shown in FIGS. 7 and 8.

Figure 9:
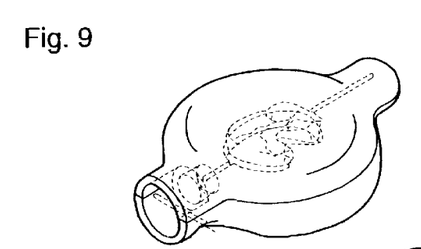
FIG. 9 is a perspective view of the two halves of the mold placed together showing the void where the mold components as shown in FIG. 2 have been removed.
Figure 10:
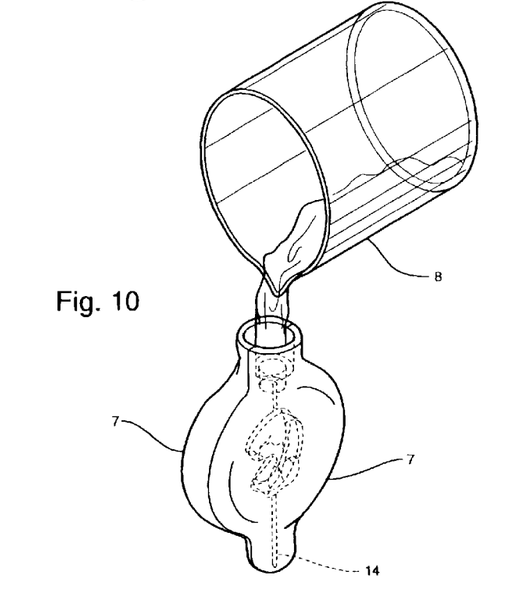
FIG. 10 is a perspective view showing the placement of the composite material in the sprue reservoir end of the mold as shown in FIG. 9.

Fib. 9 shows the mold with the duplicate space left when the was pattern (4) was removed from the mold. FIG. 10 shows the placement of the composite material. In this instance being poured into the opening made by the sprue reservoir (5). Other methods may be employed, namely, placing paste-like materials in each half of the mold (7) curing each half then placing the mold in the retention device, placing the sprue reservoir into the mold and then injecting composite into the space between the upper and lower mold sections and then curing to form one homogeneous finished restoration. Many methods of fabrication and curing using the above invention may be employed including a single shade material, strengthening inserts of various types including ceramics or glass fibers (but not limited to such materials) in keeping with the intention of the invention.

Figure 11:
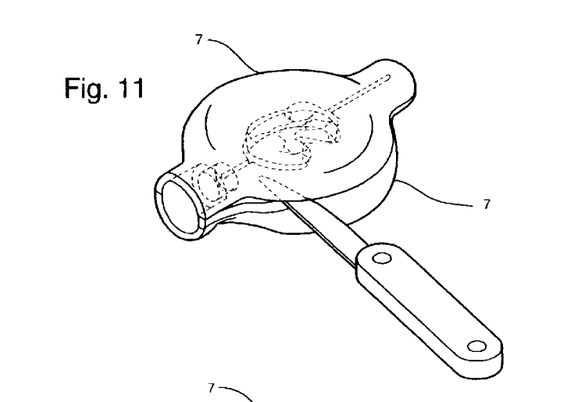
FIG. 11 is a perspective view showing the separation of the mold with an instrument subsequent to the curing of the composite material within the mold.
Figure 12:
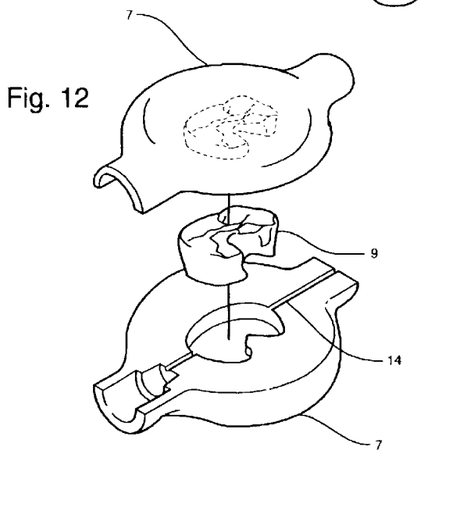
FIG. 12 is an exploded perspective view showing the cured composite being removed from the mold.

FIG. 11 shows the appropriately cured composite within the mold (7) ready to be removed. This is done by separating the retention device (1 and 2), opening the mold (7) and removing the cured restoration (9). To insure that the cured restoration is of the proper dimension, any excess composite material that was placed prior to both halves being mated together with the retention device exited through a trough (14) made from the impression of the sprue (3). Any type of overflow device may be incorporated prior to the mold (7) being made. Once the mold (7) is cut in two in FIG. 7, a trough surrounding the impression of the wax pattern (4) may be cut into one or both halves of the mold (7). This will help to insure the complete seating of mold (7) sections and the accuracy of the finished restoration.

In this invention all of the problems of the previous methods have been overcome. We use a wax pattern that fulfills the size; shape, contact, contour and occlusal harmony. This pattern is fabricated from a wax that suffers no loss of dimensional shape, is strong, can be removed from the die without alteration to check for thickness, the wax can be thickened or thinned very easily and does not adhere to the die such that removal from the die might cause the die to be broken. In addition the wax pattern can be modified such that shades of composites can be added to cusp tips or colors to fossa by removing wax in certain areas that will be filled after the initial cure.

The die spacer is a silicone spray that is blown into or on the die such that there is no loss of the size and shape of such die as can occur with other separating materials that are needed in all the other methods, if they are to be removed easily. Working with wax is and has been a mainstay of the dental laboratory dental profession. To work with it only requires a heated instrument and sharp carving instruments. This invention uses the wax in a liquid form from a dispensing device such as a dropper and is of such nature that most of the occlusal harmony is accomplished merely by closing the opposing model on the semi-solid wax. This method allows for rapid fabrication, checking for thickness and addition car deletion of material.

Once the pattern is fabricated, and has feeder tubes attached, it is surrounded by an optically self curing liquid (silicone or polyvinylsiloxane) to form a mold within a retention device. Upon curing, the mold is cut in an appropriate manner. The wax pattern is then removed and composite is pre-heated and injected into both halves of the mold with the proper color scheme. The feeder tubes which are fabricated of a material which is impervious to light energy are filled with appropriate shades of composite and the entire mold and retention device is heated to a temperature that will take advantage of the lowest viscosity of the material within the mold without causing any chemical or setting prior to the curing of the material.

After the mold and heating device are heated to the appropriate temperature. the entire mold and retention device is placed in a pressure apparatus that pressurizes the heated material to a minimum of 50–150 lbs. per sq. inch. The pressurized apparatus is then placed in a light curing device that uses intermittent light energy that cures from the surface inward. This inward curing method allows for "Directed Shrinkage" such that as the material shrinks toward the surface of the mold the pressurized material from the feeder tubes makes up any shrinkage thus allowing for a precision fit that can be duplicated over and over. This is in direct contrast to the methods where small increments are placed as the curing is unidirectional toward the light thus causing the material to shrink toward the greatest mass and away from the margins.

Following the curing of the material, it is removed from the mold, the sprues are removed and the restoration is placed in a tempering oven under vacuum at approximately 200–250 degrees F. for fifteen minutes. It is then placed on the die to check for fit and occlusal interferences. With the preceding method any adjustments are minimal. Since the wax pattern has a very smooth surface, the resulting restoration requires only buffing and no major polishing. There is complete curing to the surface without any "oxygen inhibited layer". Should the shade of the restoration be inadequate, small additions to the surface can be made without any major grinding and/or polishing. If a major color change is indicated, a new restoration can be made within minutes. An added attraction is that the lab or dentist can hold onto the mold and should the restoration fracture or come loose and is lost, a new one can be made without any other new impression and model or wax pattern.

A major advantage to the above system, is that the system is clear and the operator can see if there are any voids within the mold. While the present materials are very strong, reinforcing materials add much more strength to the material. The ideal material is various glass or ceramic fibers. It chemically bonds to the resins and is optically compatible with the shades of the material. If the glass or ceramic fibers should come to the surface, they can be polished away. This does not in any way create a defect in the restoration as the material does not wick and does not stretch. Plasma treated polyethylene or kevlar does not have a chemical compatibility with the resins of the composite. The present invention allows for any such compatible inserts of any configuration to be inserted with ease. The fact that the restoration is cured in one continuous process allows for the elimination of stresses and voids.

While but a limited number of embodiments to the present invention have been here described, it will be apparent that many variations may be made therein, without departing from the spirit of the invention defined in the following claims:

We claim:

1. A method for making a dental device or the like, which comprises:

(a) forming a pattern of the device to be made;
   (b) enclosing that pattern in a retention device having a hollow space for receiving the pattern;
   (c) placing a first settable material in the hollow of said retention device to substantially surround said pattern, and setting said first settable material to produce a unit comprising said pattern and said material;
   (d) separating said unit into at least two parts to expose said pattern, and removing said pattern from said unit, thereby producing at least one space in one of said parts, said space or spaces corresponding to said pattern;
   (e) placing a second settable material into at least one space in at least one of said parts, and closing said retention device on said at least one of said parts;
   (f) setting said second settable material, removing said unit part or parts from said retention device, opening said unit to provide access to said second set material, and removing said second set material from said unit, said removed second set material at least in part constituting said device;
   g) in which said first settable material when set is substantially optically clear material, said second settable material is light sensitive for setting, the setting of step (f) comprises the use of light as a setting agent, and said retention device is, at least in part, substantially optically clear.

2. The method of claim 1 in which said retention device is at least in part substantially optically clear and is at least in part lens-shaped over its hollow, thereby to focus the setting agent light on said unit and said pattern.

3. The method of claim 2, in which said retention device is lens-shaped on the different sides of said hollow, whereby said setting agent light is focused on a major portion of said unit and said pattern.

4. The method of claim 2, in which said retention device is lens-shaped on both sides of said hollow space.

5. The method of any of claims 1, 2, 3, in which said pattern has a sprue attached thereto before it is enclosed in said retention device, said sprue being removed from said unit along with said pattern in step (d).

6. The method of claim 5, in which said sprue carries a reservoir device accessible from the exterior of said retention device.

7. The method of claim 6, in which said retention device has an opening remote from said reservoir device through which settable material passes.

8. The method of claim 7, in which said opening in said retention device is substantially diametrically opposite said reservoir device.

9. The method of any of claims 1, 2, 3, in which said pattern has a sprue attached thereto before it is enclosed in said retention device, said sprue serving to hold said pattern in said hollow space separated from substantially all of the surface of said space, said sprue being removed from said unit along with said pattern in step (d).

10. The method of claim 9, in which said sprue carries a reservoir device accessible from the exterior of said retention device.

11. The method of claim 2, in which said retention device is substantially optically clear on both sides of said hollow.

12. The method of claim 1, in which, after step (d), composites of various shades are placed in said space in said unit before said retention device is closed.

13. The method of claim 1, in which, after step (d), each of said parts has a space corresponding to a portion of said pattern, and inserting composites of various shades in one or more of said spaces before carrying out step (e).

14. The method of claim 1 in which step (d) comprises separating said unit so that a space is formed in each of said parts, and in step (e) settable material is placed into each of said spaces and subjected to pressure to force said settable material against the surfaces of said spaces before said retention device is closed.

15. The method of claim 1, in which, in step (e), said parts of said unit are reassembled before settable material is placed therein.

16. The method of claim 1, in which, in step (e), device-modifying objects are inserted into said second settable material.

17. A retention device for use in the making of a dental device or the like with radiation-sensitive molding material which comprises at least two bodies which when assembled define (a) an internal substantially enclosed space for radiation-sensitive molding material, and (b) a passage through which said molding material may pass, the portion of said bodies communicating with said space being formed of substantially radiation clear material and shaped to produce a lens-like effect concentrating radiation into said space.

18. The retention device of claim 17, in which said portion of said bodies is shaped to produce said lens-like effect on both sides of said space.

19. A retention device for use in the making of a dental device or the like with radiation-sensitive molding material which comprises at least two bodies which when assembled define (a) an internal substantially enclosed space for radiation-sensitive molding material, and (b) a passage through which said molding material may pass, the portion of said bodies communicating with said space being formed of substantially radiation clear material.

* * * * *